United States Patent
Birkbeck

(10) Patent No.: US 8,907,134 B2
(45) Date of Patent: Dec. 9, 2014

(54) PERFUMING INGREDIENT OF THE GALBANUM FAMILY

(75) Inventor: Anthony A. Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/981,916

(22) PCT Filed: Jan. 23, 2012

(86) PCT No.: PCT/EP2012/050936
§ 371 (c)(1),
(2), (4) Date: Jul. 26, 2013

(87) PCT Pub. No.: WO2012/110281
PCT Pub. Date: Aug. 23, 2012

(65) Prior Publication Data
US 2013/0310293 A1      Nov. 21, 2013

(30) Foreign Application Priority Data

Feb. 17, 2011   (EP) ..................................... 11154754

(51) Int. Cl.
*C07C 49/225*   (2006.01)
*C07C 49/557*   (2006.01)
*C11B 9/00*     (2006.01)
*C11D 3/50*     (2006.01)

(52) U.S. Cl.
CPC ............. *C07C 49/557* (2013.01); *C11B 9/0034* (2013.01); *C11D 3/50* (2013.01); *C07C 2101/16* (2013.01)
USPC ............................................ 568/377; 512/24

(58) Field of Classification Search
USPC ............................................ 512/24; 568/377
See application file for complete search history.

(56) References Cited

U.S. PATENT DOCUMENTS

| | | | |
|---|---|---|---|
| 4,147,672 A | 4/1979 | Schulte-Elte et al. | |
| 7,790,662 B2* | 9/2010 | Sahin Topkara et al. | 510/101 |
| 8,022,030 B2* | 9/2011 | Berthier et al. | 512/1 |
| 2011/0077188 A1* | 3/2011 | Ouali et al. | 512/2 |

FOREIGN PATENT DOCUMENTS

EP   0 913 383 A1   5/1999

OTHER PUBLICATIONS

International Search Report and Written Opinion, application PCT/EP2012/050936, mailed Apr. 3, 2012.
Mihovilovic et al., Org. Chem. 2001, 66, 733-738.

\* cited by examiner

*Primary Examiner* — John Hardee
(74) *Attorney, Agent, or Firm* — Winston & Strawn LLP

(57) ABSTRACT

The present invention relates to 1-(5-ethyl-5-methyl-1-cyclohexen-1-yl)-4-penten-1-one and its use as perfuming ingredient.

6 Claims, No Drawings

PERFUMING INGREDIENT OF THE GALBANUM FAMILY

TECHNICAL FIELD

The present invention relates to the field of perfumery. More particularly, it concerns 1(5-ethyl-5-methyl-1-cyclohexen-1-yl)-4-penten-1-one and its use as perfuming ingredient. Moreover, the present invention comprises the invention's compound as part of a perfuming composition or of a perfuming consumer product.

PRIOR ART

Galbanum oil is a natural perfuming ingredient highly appreciated by perfumers for its green character. However, its use is limited by a high cost. The perfumery industry has been looking and still searches for synthetic replacers having an odor as close as possible and being as substantive as possible. By the term "substantive" it is meant the strength and the olfactive performance of an odor note over a defined period of time.

Although, to the best of our knowledge, the invention's compound is novel, for the sake of the present invention, two prior art documents are of interest:

U.S. Pat. No. 4,147,672 discloses perfuming ingredients having green, herbal and fruity notes and reminiscent of galbanum oil and defines a very broad general formula including the present compound. However the preferred compounds disclosed herein are all gem-dimethyl, 3,4-dimethyl or 3,3,4-trimethyl compounds, and moreover nothing is mentioned about substantivity.

The best product corresponding to said patent is commercialized under the trademark Neobutenone® alpha (1-(5,5-dimethyl-1-cyclohexen-1-yl)-4-penten-1-one; sold by Firmenich SA) and is described as having a green-metallic, fruity (pineapple) and floral (hyacinth) odor reminiscent of galbanum.

EP 913383 discloses perfuming ingredients having a fresh green, metallic, green-galbanum and pineapple odor, reminiscent of galbanum oil. Said document clearly specifies that replacing the gem-dimethyl group of Neobutenone® alpha with a spiro ring "strongly enhances the substantivity of the product without changing the perception and the type of odor".

The best product corresponding to said patent is commercialized under the trademark Spirogalbanone® (1-spiro(4.5)-7/6-decen-7-yl-4 penten-1-one; sold by Givaudan S A) and is described as having a powerful, substantive green galbanum note combined with fruity (pineapple) facets.

DESCRIPTION OF THE INVENTION

We have now surprisingly discovered that a compound of formula

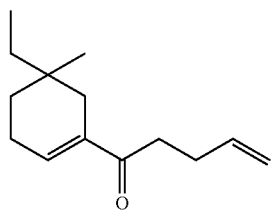

in the form of any one of its enantiomers or a mixture thereof; can be used as perfuming ingredient, for instance to impart odor notes of the galbanum type.

For the sake of clarity, by the expression "any one of its enantiomers", it is meant the normal meaning understood by a person skilled in the art, e.g. that the invention's compound can be a pure enantiomer or racemate.

The particularly surprising aspect of the present invention is that the compound (I) possesses surprising organoleptic properties in the sense that it combines an improved odor profile with an improved substantivity despite having a structure clearly described as unfavorable for such properties.

1-(5-Ethyl-5-methyl-1-cyclohexen-1-yl)-4-penten-1-one has been surprisingly found to have a superior odor and a superior substantivity compared to the above-cited prior art ingredients.

The odor of the invention's compound is described as being a complex green, metallic galbanum note with an elegant earthy, pyrazinic aspect reminding of the earthy aspect of fig.

The whole olfactive character of the invention's compound, when compared to that of Neobutenone® alpha or Spirogalbanone®, clearly appears as to be the closest odor in respect of galbanum oil.

In particular, 1-(5-ethyl-5-methyl-1-cyclohexen-1-yl)-4-penten-1-one distinguishes itself from Neobutenone® alpha by having a green note more complex, more earthy, heavy while the Neobutenone® alpha possesses a green note significantly more herbal and fresh. 1-(5-Ethyl-5-methyl-1-cyclohexen-1-yl)-4-penten-1-one distinguishes itself from Spirogalbanone® by lacking the typical glycolate, pineapple green sweet character of the latter, as well as by lacking the fatty aspect of Spirogalbanone®.

In other words, 1-(5-ethyl-5-methyl-1-cyclohexen-1-yl)-4-penten-1-one is characterized by a very close galbanum character, of the earthy pyrazine type, while Neobutenone® alpha deviates from said galbanum character by having a fresher and acidic note and Spirogalbanone® deviates from said galbanum character by having a fruity, sweety note.

Moreover, and even more surprisingly, 1-(5-ethyl-5-methyl-1-cyclohexen-1-yl)-4-penten-1-one not only possesses a specific character which distinguishes itself from the prior art ones, but also possesses a significantly improved sustantivity, as shown in the examples. Indeed, a panel of ten perfumers, using standard procedures, scored the invention's compound as having a substantivity far above that of its closest analogue Neobutenone® alpha and significantly higher than the one of Spirogalbanone®.

The present invention fulfills the above-mentioned need of the perfumery industry by providing a new compound showing an improved galbanum resemblance and an improved substantivity while having a structure clearly described in the prior art as unfavorable for such goal.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids:Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

The invention's compounds can be prepared according to a method as described in the Examples.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of the Compound of Formula (I)

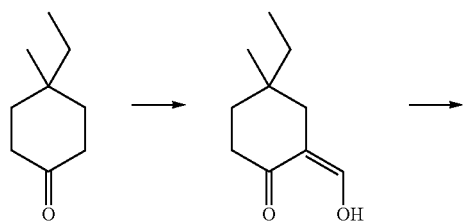

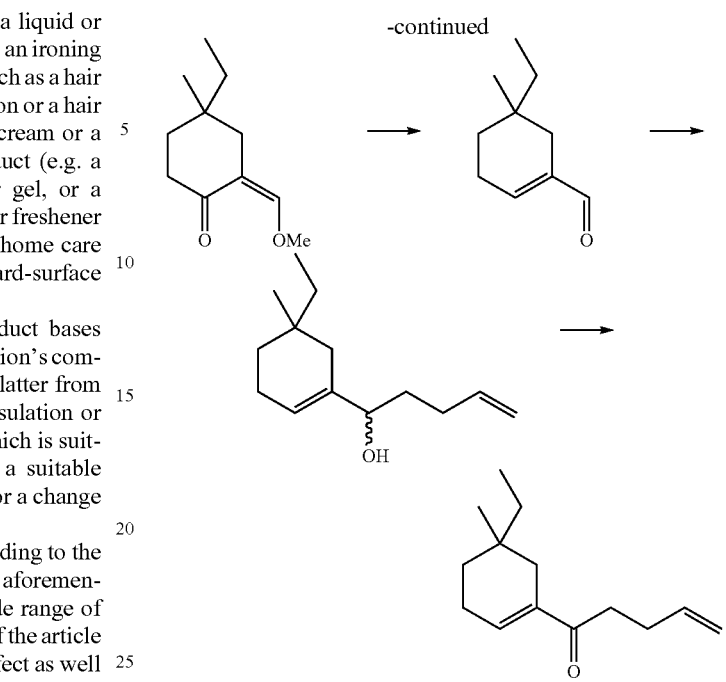

Step 1:

To a mechanically stirred solution of ethyl formate (65 g, 878 mmol) in dry ether (200 ml) cooled to 5° C. was added solid sodium methoxide (46 g, 852 mmol) in small portions maintaining the temperature<10° C. throughout the addition. A solution of 4-ethyl-4-methyl cyclohexanone (preparation: *J. Org. Chem.*, 2001, 66, 733) (85 g, 607 mmol) in dry ether (400 ml) was added slowly dropwise over 1 hour. A further portion of dry ether (100 ml) was added. After 3 hours at ambient temperature, acetic acid (25 ml) was added slowly dropwise, and then the reaction mixture poured onto a mixture of ice/water, extracted with ether (2×), washed the combined organic phase with sodium bicarbonate (2×), brine, dried over Na$_2$SO$_4$, filtered and the solvents removed in vacuo. The crude formyl ketone was distilled 0.3 mbar at 47-49° C. to give the desired formyl ketone, 75.9 g.

$^{13}$C NMR: 187.1 (CH), 185.2 (q), 107 (q), 35.2 (CH$_2$), 32.7 (CH$_2$), 32.0 (q), 31.6 (CH$_2$), 28.6 (CH$_3$), 23.4 (CH$_3$), 8.0 (CH$_3$).

Steps 2 & 3:

pTSA (1.5 g, cat.) was added in one portion to a well stirred solution of the enol obtained in step 1 (75 g, 446 mmol), methanol (150 ml) and trimethyl orthoformate (66 g). The reaction mixture was then stirred for a further 30 minutes at ambient temperature, then poured into saturated NaHCO$_3$, extracted with ether, washed organic phase with brine (3×), dried over Na$_2$SO$_4$, filtered and the solvents removed in vacuo. The residue was further purified by Vigreux column distillation 0.24 mbar at 84-94° C. to give the enol ether 43.7 g, 54% that was used directly in the next step without further purification. A solution of the enol ether (47.7 g, 260 mmol) in dry ether (300 ml) was added slowly dropwise to a mechanically stirred suspension of LiAlH$_4$ (5.5 g, 144.7 mmol) in dry ether (200 ml) at ambient temperature. The suspension was stirred at ambient temperature overnight, then cooled to 5° C. in an ice bath and water (5.5 ml) was added very cautiously dropwise, vigorous exothermic reaction, followed by 15% NaOH (5.5 ml) then finally water (16.5 ml). A large spoonful of anhydrous MgSO$_4$ was added and the suspension stirred for a further 1 hour at ambient temperature, then filtered and the solvents removed in vacuo to yield a colourless oil, 55 g, yield=100% used without further purification in the next step.

A solution of the hydroxyl enol ether (55.0 g, 260 mmol) in toluene (600 ml) containing pTSA (1.0 g cat.) was stirred at ambient temperature for 2 hours. Added saturated $NaHCO_3$ (50 ml), extracted the aqueous phase with ether (2×), washed with water (3×), dried over $Na_2SO_4$, filtered and the solvents removed in vacuo. The residue was further purified by vigreux distillation 0.5 mbar at 27-29° C. gave the desired aldehyde 22 g, yield=56%.

$^{13}C$ NMR: 194.6 (CH), 150.6 (CH), 140.7 (q), 33.5 ($CH_2$), 33.0 ($CH_2$), 32.6 ($CH_2$), 30.9 (q), 24.2 ($CH_2$), 23.5 ($CH_3$), 7.8 ($CH_3$).

Step 4:

A solution of 4-bromo-1-butene (19.5 g, 144 mmol) in dry ether (80 ml) was added slowly dropwise to a stirred suspension of Mg turnings (3.05 g, 127 mmol) in dry ether (5 ml) containing dibromo ethane (3 drops). After the complete disappearance of the magnesium metal, a solution of the aldehyde (13.5 g, 88.8 mmol) in dry ether (80 ml) was added slowly dropwise and allowed to attain reflux. Stirred for a further 15 minutes after the addition was complete then poured into iced water, re extracted with ether (2×), washed with saturated $NH_4Cl$, brine, dried over $Na_2SO_4$, then filtered and the solvents removed in vacuo. The crude alcohol as a 1:1 mixture of diastereoisomers 18.9 g was used directly in the next step without further purification.

$^{13}C$ NMR: 138.53 (CH), 138.48 (CH), 122.2 (CH), 122.1 (CH), 114.7 ($CH_2$), 76.2 (CH), 76.1 (CH), 35.6, 35.5, 34.0, 33.9, 33.8, 33.3, 33.0, 32.9 ($CH_2$), 31.34, 31.33 (q), 24.0, 23.5 ($CH_3$), 22.6 ($CH_2$), 7.92, 7.90 ($CH_3$).

Step 5:

A solution of the alcohol (18.0 g, 86.5 mmol) in pentane (200 ml) was added rapidly dropwise to a mechanically stirred suspension of $MnO_2$ (200 g, 2.4 mol) in pentane (500 ml). The brown suspension was stirred for 2 hours at ambient temperature, then filtered through a plug of celite (10 cm), rinsed with pentane. The filtrate was concentrated in vacuo to yield the crude ketone 13.0 g as an oil. Further purification by bulb to bulb distillation, 0.5 mbar at 150° C. gave the desired ketone, 12.2 g, yield=68%.

$^{13}C$ NMR: 200.8 (q), 138.8 (CH), 138.1 (q), 137.7 (CH), 114.9 ($CH_2$), 36.4, 35.0, 33.6, 31.9 ($CH_2$), 31.2 (q), 28.8 ($CH_2$), 23.8 ($CH_2$), 23.7 ($CH_3$), 7.8 ($CH_3$).

Example 2

Preparation of a Perfuming Composition

A perfuming composition for encapsulation and introduction into a detergent, of the fruity/green type, was prepared by admixing the following ingredients:

| Parts by weight | Ingredient |
| --- | --- |
| 1200 | Hexyl acetate |
| 400 | MNA aldehyde |
| 40 | Calone ® [1] |
| 250 | Coumarine |
| 80 | Damascenone |
| 200 | Damascone Alpha |
| 40 | Delphone[2] |
| 250 | Diphenyloxide |
| 40 | Ethylpraline |
| 400 | Hedione ® [3] |
| 200 | Hivernal ® Neo[4] |

-continued

| Parts by weight | Ingredient |
| --- | --- |
| 2000 | Iralia ® Total[5] |
| 40 | (Z,Z)-3,6-nonadien-1-ol |
| 200 | Gamma nonalactone |
| 2400 | Phenylhexanol |
| 800 | Sclareolate ® [6] |
| 280 | Veloutone[7] |
| 80 | 2-Methyl-3-hexanone oxime[8] |
| 200 | 10%* Violettyne [9] |
| 800 | 3Z-hexenyl 3Z-hexenoate[8] |
| 9900 | |

*in isopropyle myristate
[1] 7-methyl-2H,4H-1,5-benzodioxepin-3-one; origin: Firmenich SA, Geneva, Switzerland
[2] 2-pentyl-cyclopentanone; origin: Firmenich SA, Geneva, Switzerland
[3] methyl cis-dihydrojasmonate; origin: Firmenich SA, Geneva, Switzerland
[4] 3-(3,3/1,1-dimethyl-5-indanyl)propanal; origin: Firmenich SA, Geneva, Switzerland
[5] mixture of methylionones isomers; origin: Firmenich SA, Geneva, Switzerland
[6] propyl (S)-2-(1,1-dimethylpropoxy)propanoate; origin: Firmenich SA, Geneva, Switzerland
[7] 2,2,5-trimethyl-5-pentyl-1-cyclopentanone; origin: Firmenich SA, Geneva, Switzerland
[8] origin: Firmenich SA, Geneva, Switzerland
[9] 1,3-undecadien-5-yne; origin: Firmenich SA, Geneva, Switzerland The addition of 100 parts by weight of 1-(5-ethyl-5-methyl-1-cyclohexen-1-yl)-4-penten-1-one to the above-described composition imparted to the latter a strong galbanum note together with an aspect reminding of fig.

When to the above-described composition were added 100 parts by weight of Neobutenone® alpha, it was still imparted a note in the galbanum direction but fresher, and more herbal, citrusy, clearly less galbanum oil than the one imparted by the invention's compound.

When to the above-described composition were added 100 parts by weight of Spirogalbanone®, it was still imparted a note in the galbanum direction but fattier, more glycolate/pineapple, clearly less galbanum oil than the one imparted by the invention's compound.

Substantivity Test

Three different perfumed detergents were obtained by adding into 100 g of a standard unperformed detergent power 0.2% w/w of A) the invention compound, B) Neobutenone® alpha, C) Spirogalbanone®.

Each of the three different perfumed detergents was used to wash at 40° C., in a standard washing machine, 3 cotton linens of about 25 cm/25 cm. The different sets of linen were then blind evaluated by a panel of 10 perfumers for their odor substantivity when still humid (just after rinsing and spinning) and when dry after 24 hours (air dried linen).

The odor impart or strength was scored on the basis of a scale from 0 to 10, 10 being the highest possible score. The test was repeated three times and all tests were consistent. Table 1 reports the score obtained:

TABLE 1

| Substantivity data | | |
| --- | --- | --- |
| Detergent with | Humid | Dry |
| Neobutenone ® alpha | 9.5 | 3.9 |
| Spirogalbanone ® | 7.2 | 5.0 |
| Invention's compound | 8 | 5.5 |

These olfactive differences described above were still observable on both humid and linen (i.e. even 24 hours after the washing). Moreover Table 1 shows, from a substantivity stand point, that when:

comparing the invention's compound with Neobutenone® alpha, clearly the invention's compound is more performing (stronger odor impart) than its prior art closest analogue on the long term (dry linen), thus showing strongly improved substantivity;

comparing the invention's compound with Spirogalbanone®, clearly the invention's compound is more performing (stronger odor impart) than its prior art analogue at any moment of the test, thus showing improved substantivity even toward said ingredient ant this despite the fact the invention's compound does not possess a prerequisite taught by the prior art.

Example 3

Preparation of a Perfuming Composition

A perfuming composition for powder detergent was prepared by admixing the following ingredients:

| Parts by weight | Ingredient |
| --- | --- |
| 100 | Hexyl acetate |
| 500 | Benzyl acetate |
| 100 | Geranyl acetate |
| 100 | Phenylethyl acetate |
| 100 | Styrallyl acetate |
| 500 | Verdyl acetate |
| 100 | Anisic aldehyde |
| 450 | Hexylcinnamic aldehyde |
| 20 | Aldehyde Supra |
| 100 | Undecylic aldehyde |
| 50 | Ethyl 2-methyl-pentanoate |
| 50 | Methyl benzoate |
| 40 | Bourgeonal ® [1] |
| 50 | Cetalox ® [2] |
| 20 | Cis-3-Hexenol |
| 250 | 4-Cyclohexyl-2-methyl-2-butanol[3] |
| 30 | Damascone Delta |
| 1500 | Dihydromyrcenol |
| 50 | Ethylvanilline |
| 80 | Eugenol |
| 100 | Fructalate ™ [4] |
| 600 | 70%** Galaxolide ® [5] |
| 500 | 60%* Geraniol |
| 250 | Hedione ® [6] |
| 80 | Allyl heptanoate |
| 20 | 10%* 1-Phenylvinyl acetate[3] |
| 100 | Ionone Beta |
| 500 | Iralia ® Total[7] |
| 500 | Iso E ® Super[8] |
| 100 | Lavandin Grosso |
| 50 | Lemonile ® [9] |
| 200 | Lilial ® [10] |
| 10 | 1-(2,2,3,6-Tetramethyl-cyclohexyl)-3-hexanol[3] |
| 50 | Isopropyl methylbutyrate |
| 20 | 1-Methoxy-4-methylbenzene |
| 50 | Muscenone ™ Delta[11] |
| 100 | Nirvanol ® [12] |
| 20 | 10%* Cis-2-methyl-4-propyl-1,3-oxathiane[3] |
| 20 | Rose oxide |
| 50 | Patchouli oil |
| 40 | Petitgrain |
| 400 | Phenethylol |
| 400 | Hexyl salicylate |
| 350 | Sclareolate ® [13] |
| 50 | 1%* (Z)-4-Dodecenal |
| 200 | Terpenes Orange |
| 300 | Terpineol |
| 100 | Gamma undecalactone |
| 150 | Undecavertol ® [14] |
| 300 | Verdox ® [15] |
| 50 | 10%** Violettyne[16] |

-continued

| Parts by weight | Ingredient |
| --- | --- |
| 50 | 3Z-hexenyl 3Z-hexenoate[3] |
| 50 | 2,4-Dimethyl-3-cyclohexene-1-carbaldehyde[3] |
| 9950 | |

*in dipropyleneglycol
**in isopropyle myristate
[1] 3-(4-tert-butylphenyl)propanal; origin: Givaudan SA, Vernier, Switzerland
[2] dodecahydro-3a,6,6,9a-tetramethyl-naphtho[2,1-b]furan; origin: Firmenich SA, Geneva, Switzerland
[3] origin: Firmenich SA, Geneva, Switzerland
[4] diethyl 1,4-cyclohexane dicarboxylate; origin: Givaudan SA, Vernier, Switzerland
[5] 1,3,4,6,7,8-hexahydro-4,6,6,7,8,8-hexamethyl-cyclopenta-g-2-benzopyrane; origin: Firmenich SA, Geneva, Switzerland
[6] methyl cis-dihydrojasmonate; origin: Firmenich SA, Geneva, Switzerland
[7] methyl cis-dihydrojasmonate; origin: Firmenich SA, Geneva, Switzerland
[8] 1-(octahydro-2,3,8,8-tetramethyl-2-naphthalenyl)-1-ethanone; origin: International Flavors & Fragrances, USA
[9] 3,7-dimethyl-2/3,6-nonadienenitrile; origin: Givaudan SA, Vernier, Switzerland
[10] 3-(4-tert-butylphenyl)-2-methylpropanal; origin: Givaudan SA, Vernier, Switzerland
[11] 3-methyl-5-cyclopentadecen-1-one; origin: Firmenich SA, Geneva, Switzerland
[12] 3,3-dimethyl-5-(2,2,3-trimethyl-3-cyclopenten-1-yl)-4-penten-2-ol; origin: Firmenich SA, Geneva, Switzerland
[13] propyl (S)-2-(1,1-dimethylpropoxy)propanoate; origin: Firmenich SA, Geneva, Switzerland
[14] 4-methyl-3-decen-5-ol; origin: Givaudan SA, Vernier, Switzerland
[15] 2-tert-butyl-1-cyclohexyl acetate; origin: International Flavors & Fragrances, USA
[16] 1,3-undecadien-5-yne; origin: Firmenich SA, Geneva, Switzerland The addition of 50 parts by weight of 1-(5-ethyl-5-methyl-1-cyclohexen-1-yl)-4-penten-1-one to the above-described composition imparted to the latter a nice green note exalting the violets leaves tonality and reinforcing the fruity aspects.

The addition at the same amount of the prior art analogues introduced unbalanced effects. In the case of Neobutenone® alpha, the fragrance was too greeny, pushing the citrus aspects, while in the case of Spirogalbanone® the new fragrance was too heavy, less sparkling.

What is claimed is:
1. A compound of formula

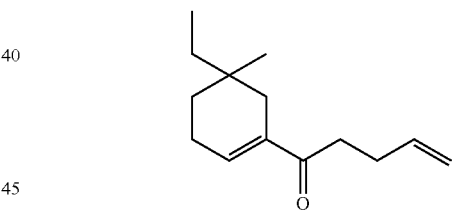

in the form of any one of its enantiomers or a mixture thereof.

2. A method to confer, enhance, improve or modify the odor properties of a perfuming composition or of a perfumed article, which method comprises adding to said composition or article an effective amount of at least a compound of formula (I) as defined in claim 1.

3. A perfuming composition comprising
 i) at least one compound of formula (I), as defined in claim 1;
 ii) at least one ingredient selected from the group consisting of a perfumery carrier and a perfumery base; and
 iii) optionally at least one perfumery adjuvant.

4. A perfuming consumer product comprising:
 i) at least one compound of formula (I), as defined in claim 1; and
 ii) a perfumery consumer base.

5. A perfuming consumer product according to claim 4, wherein the perfumery consumer base is a perfume, a fabric care product, a body-care product, an air care product or a home care product.

6. A perfuming consumer product according to claim 5, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *